United States Patent
Mou et al.

(10) Patent No.: US 10,955,320 B2
(45) Date of Patent: *Mar. 23, 2021

(54) GAS DETECTING DEVICE FOR MONITORING AIR QUALITY IN A GAS TRANSPORTATION DEVICE

(71) Applicant: Microjet Technology Co., Ltd., Hsinchu (TW)

(72) Inventors: Hao-Jan Mou, Hsinchu (TW); Shih-Chang Chen, Hsinchu (TW); Ching-Sung Lin, Hsinchu (TW); Yung-Lung Han, Hsinchu (TW); Chi-Feng Huang, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 146 days.

This patent is subject to a terminal disclaimer.

(21) Appl. No.: 16/233,820

(22) Filed: Dec. 27, 2018

(65) Prior Publication Data

US 2019/0265132 A1    Aug. 29, 2019

(30) Foreign Application Priority Data

Feb. 27, 2018  (TW) ................................ 107106632

(51) Int. Cl.
  *G01N 1/24*  (2006.01)
  *G01N 1/22*  (2006.01)
  *G01N 33/00*  (2006.01)

(52) U.S. Cl.
  CPC ............. *G01N 1/24* (2013.01); *G01N 1/2273* (2013.01); *G01N 33/0009* (2013.01);
  (Continued)

(58) Field of Classification Search
  None
  See application file for complete search history.

(56) References Cited

U.S. PATENT DOCUMENTS 9,321,640 B2    4/2016   Tsangaris et al.
10,620,106 B2 *  4/2020   Mou .................. G01N 15/0211
(Continued)

FOREIGN PATENT DOCUMENTS

CN    102564949 A    7/2012
CN    205538890 U *  8/2016    ............... G01N 1/24
(Continued)

OTHER PUBLICATIONS

Extended European Search Report, dated Aug. 8, 2019, for European Application No. 19151000.7.

*Primary Examiner* — Harshad R Patel
(74) *Attorney, Agent, or Firm* — Birch, Stewart, Kolasch & Birch, LLP (57) ABSTRACT

A gas detecting device includes a casing, a gas transportation actuator, a gas detector and a driving module. The casing has an inlet, an outlet and an accommodation slot. The inlet and the outlet are in fluid communication with each other, and the accommodation slot is disposed under the inlet and is in fluid communication with the inlet. The gas transportation is disposed within and seals the accommodation slot, and the gas transportation actuator is enabled to introduce air thereinto through the inlet and discharge the air through the outlet. The gas detector is configured to detect an amount of a specific gas in the air introduced through the inlet. The driving module controls the actuations of the gas transportation actuator and the gas detector, so that the gas detector detects the amount of the specific gas in the air.

15 Claims, 11 Drawing Sheets

(52) U.S. Cl.
CPC ..... *G01N 33/0047* (2013.01); *G01N 33/0062* (2013.01); *G01N 33/0063* (2013.01); *G01N 33/0073* (2013.01)

(56) References Cited

U.S. PATENT DOCUMENTS

| | | | |
|---|---|---|---|
| 10,775,289 B2* | 9/2020 | Mou | G01N 15/1459 |
| 2014/0377099 A1* | 12/2014 | Hsueh | F04B 49/22 |
| | | | 417/413.2 |
| 2016/0076530 A1* | 3/2016 | Chen | F04B 43/046 |
| | | | 417/413.2 |
| 2019/0187035 A1* | 6/2019 | Mou | G01N 15/06 |
| 2019/0234851 A1* | 8/2019 | Mou | G01N 15/1459 |

FOREIGN PATENT DOCUMENTS

| | | | |
|---|---|---|---|
| CN | 107037178 A * | 8/2017 | |
| CN | 206421104 U * | 8/2017 | |
| EP | 2733484 A1 | 5/2014 | |
| TW | 201221952 A | 6/2012 | |
| TW | M549939 U | 10/2017 | |
| TW | M553417 U | 12/2017 | |
| WO | WO 2008/024138 A1 | 2/2008 | |
| WO | WO 2012/154029 A1 | 11/2012 | |

* cited by examiner

GAS DETECTING DEVICE FOR MONITORING AIR QUALITY IN A GAS TRANSPORTATION DEVICE

FIELD OF THE INVENTION

The present disclosure relates to a gas detecting device, and more particularly to a gas detecting device of enhancing the efficiency of detecting by a gas transportation actuator.

BACKGROUND OF THE INVENTION

Nowadays, people pay much attention to the air quality in the environment. For example, it is important to monitor carbon monoxide, carbon dioxide, volatile organic compounds (VOC), Particulate Matter 2.5 (PM2.5), nitric oxide, sulfur monoxide, and so on. The exposure of these substances in the environment will cause human health problems or even harm the life. Therefore, it is important for every country to improve the air quality.

Generally, it is feasible to use an environmental sensor to monitor the air quality in the environment. If the environmental sensor is capable of immediately providing people with the monitored information relating to the environment for caution, it may help people escape or prevent from the injuries and influence on human health caused by the exposure of the substances described above in the environment. In other words, the environmental sensor is suitably used for monitoring the ambient air in the environment.

Nowadays, a large-scale environmental monitoring base station is provided to monitor the ambient air quality. However, the large-scale environmental monitoring base station is only suitable for monitoring the ambient air quality near the environmental monitoring base station. If the large-scale environmental monitoring base station is used to monitor the air quality in a small area where human activities exist (e.g., the indoor air quality and the ambient air surrounding us), the monitoring result is usually not accurately and quickly acquired. Consequently, the air quality cannot be effectively monitored everywhere and at any time.

As mentioned above, the air quality cannot be measured and improved by the current air quality monitoring system everywhere and at any time. Moreover, even if the process of improving the air quality is performed, the current air quality monitoring system cannot immediately learn whether the improved air quality is acceptable. If the air quality has been improved but the improved air quality is not recognized, the process of improving the air quality has to be continuously performed. Under this circumstance, the process of improving the air quality is workless and consumes energy.

Therefore, there is a need of providing a gas detecting device for monitoring the air quality in real time, increasing the monitoring accuracy, immediately monitoring the air quality everywhere and at any time, and enabling the air quality notification mechanism and the air quality processing mechanism.

SUMMARY OF THE INVENTION

An object of the present disclosure provides a gas detecting device in which a gap between a piezoelectric actuator and a resonance plate can be adjusted with precision, by which the gas can be stably transported with efficiency.

An object of the present disclosure provides a gas detecting device for improving a moving speed of an air and an efficiency of detecting the air by the gas transportation actuator.

In accordance with an aspect of the present disclosure, a gas detecting device is provided. The gas detecting device includes a casing, a gas transportation actuator, a gas detector and a driving module. The casing has an inlet, an outlet and an accommodation slot. The inlet and the outlet are in fluid communication with each other, and the accommodation slot is disposed under the inlet and is in fluid communication with the inlet. The gas transportation actuator is disposed within and seals the accommodation slot, and the gas transportation actuator is enabled to introduce air thereinto through the inlet and discharge the air through the outlet. The gas detector is configured to detect an amount of a specific gas in the air introduced through the inlet. The driving module is disposed within the casing and configured to control actuations of the gas transportation actuator and the gas detector. In response, the gas detector detects the amount of the specific gas in the air.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
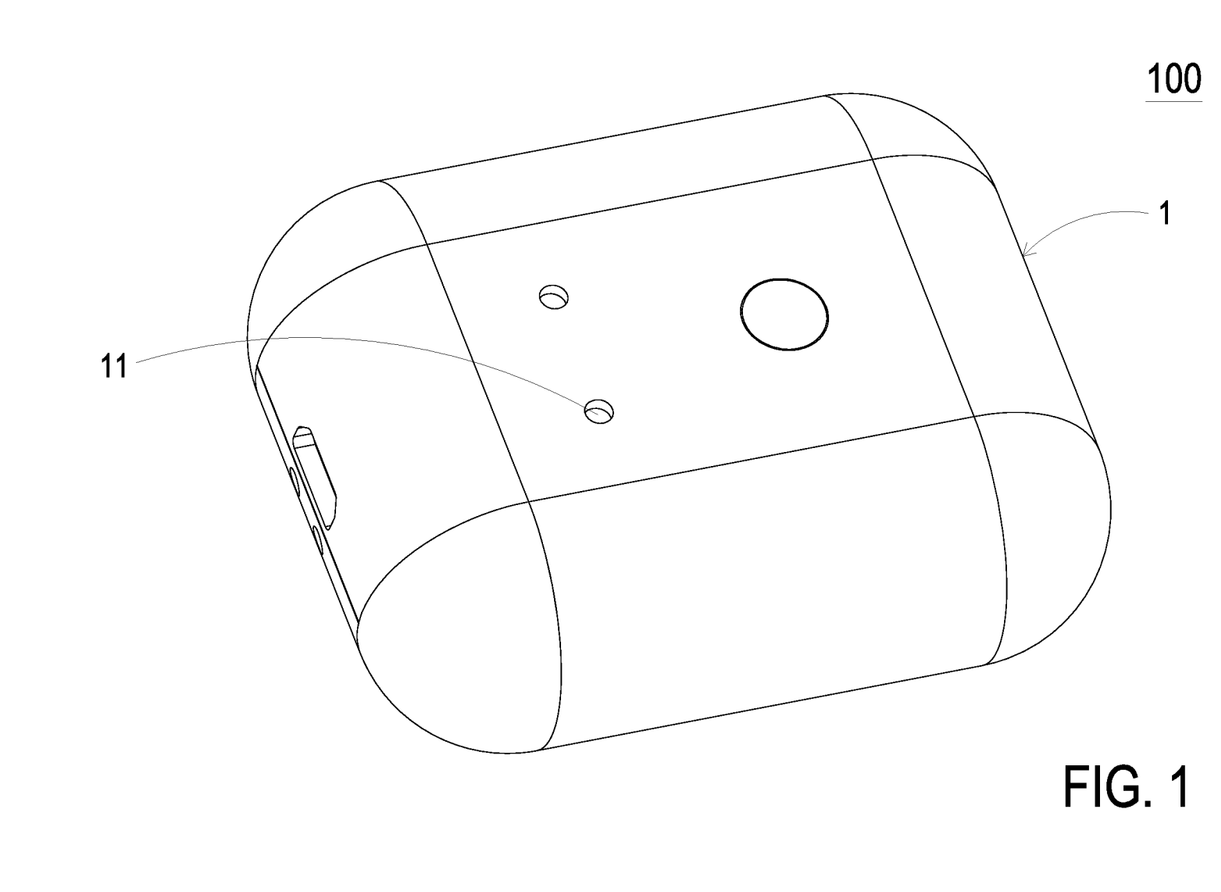
FIG. 1 is a schematic perspective view illustrating a gas detecting device according to an embodiment of the present disclosure.
Figure 2:
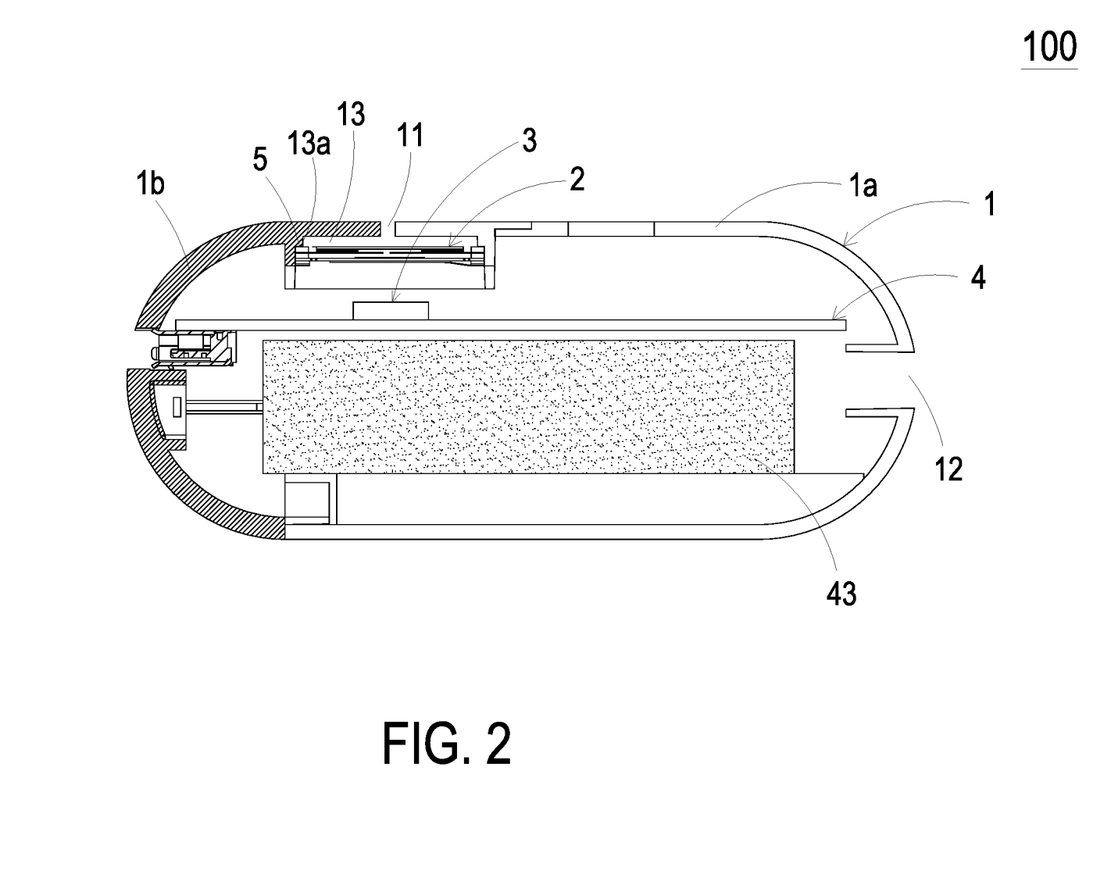
FIG. 2 is a schematic cross-sectional view illustrating the gas detecting device according to the embodiment of the present disclosure.
Figure 3:
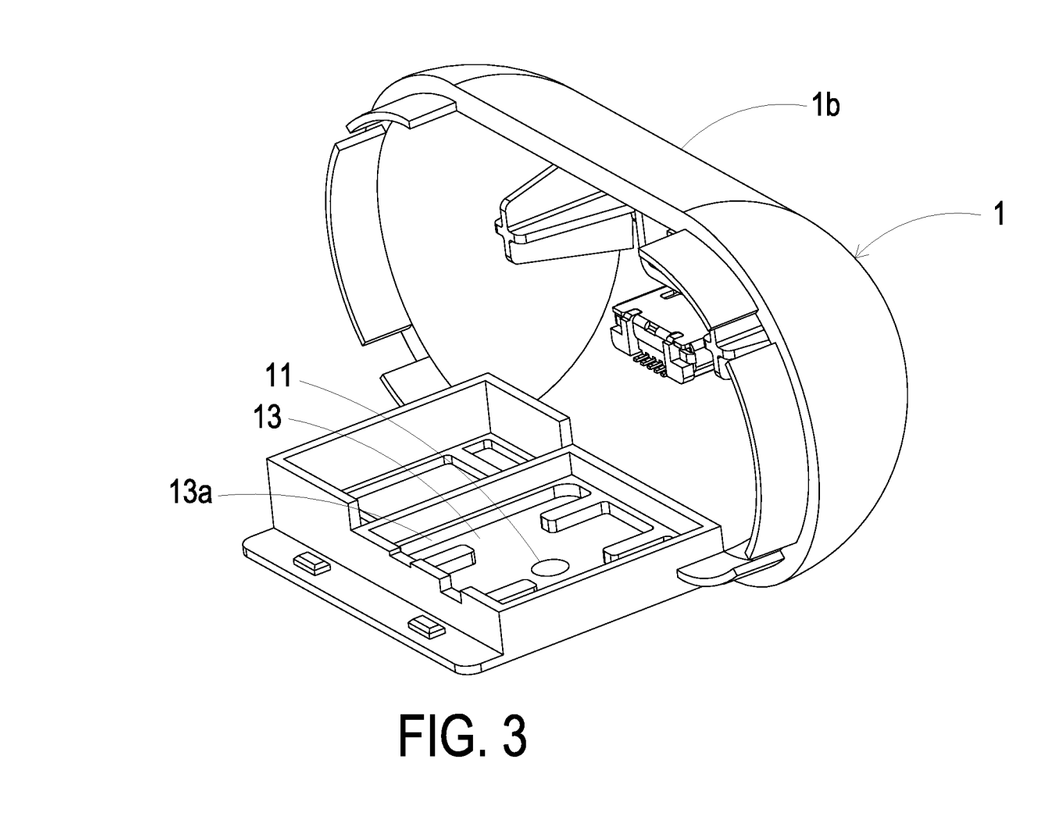
FIG. 3 is a schematic perspective view illustrating a casing while the gas detecting device of FIG. 1 is not equipped with a gas transportation actuator.
Figure 4:
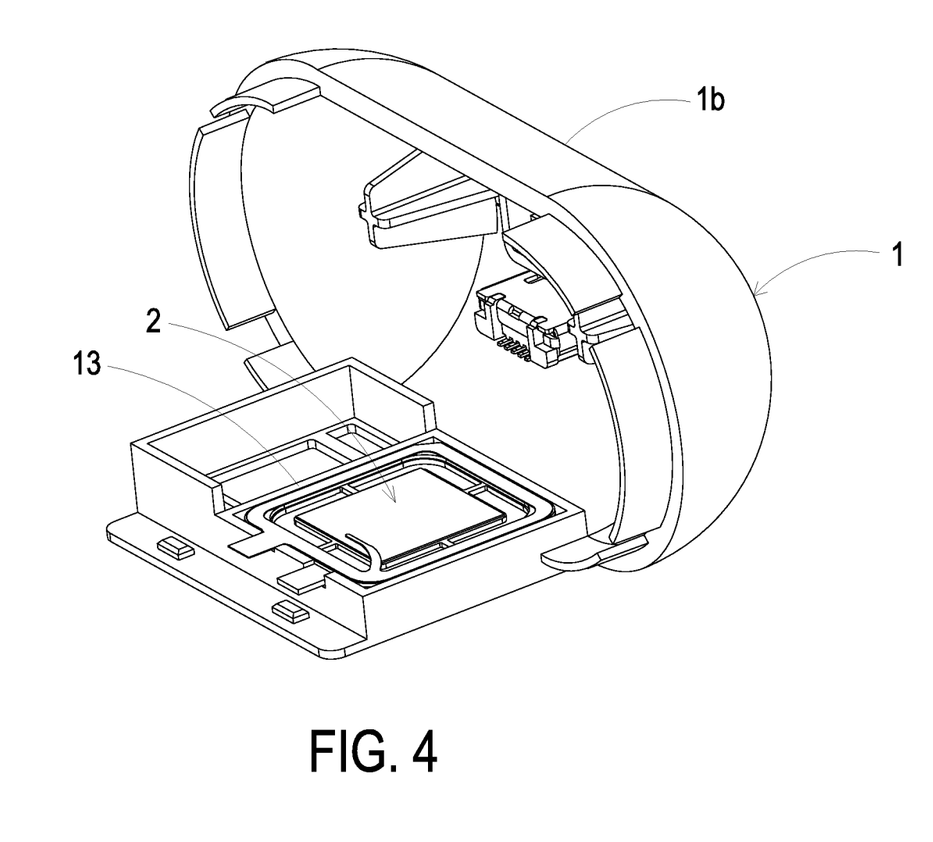
FIG. 4 is a schematic perspective view illustrating the casing while the gas detecting device of FIG. 1 is equipped with the gas transportation actuator.

Please refer to FIG. 2. The present discourse provides a gas detecting device 100 including at least one casing 1, at least one gas transportation actuator 2, at least one gas detector 3, at least one driving module 4, at least one inlet 11, at least one outlet 12 and at least one accommodation slot 13. The number of the casing 1, the gas transportation actuator 2, the detector 3, the driving module 4, the inlet 11, the outlet 12 and the accommodation slot 13 is exemplified by one for each in the following embodiments but not limited thereto. It is noted that each of the casing 1, the gas transportation actuator 2, the detector 3, the driving module 4, the inlet 11, the outlet 12 and the accommodation slot 13 can also be provided in plural numbers.

The present disclosure provides a gas detecting device. Please refer to FIGS. 1 to 4. The gas detecting device 100 includes a casing 1, a gas transportation actuator 2, a gas detector 3 and a driving module 4. The casing 1 includes an inlet 11, an outlet 12 and an accommodation slot 13. The inlet 11 and the outlet 12 are in fluid communication with each other. The accommodation slot 13 is disposed under the inlet 11 and is in fluid communication with the inlet 11, and the accommodation slot 13 is in fluid communication with the outlet 12. The accommodation slot 13 is located between the inlet 11 and the outlet 12 for allowing the inlet 11 and the outlet 12 to be in fluid communication with each other through the accommodation slot 13. The gas transportation actuator 2 is disposed within the accommodation slot 13. In this embodiment, the accommodation slot 13 is sealed while the gas transportation actuator 2 is disposed within the accommodation slot 13. The gas transportation actuator 2 seals the edge of the accommodation slot 13. As the gas transportation actuator 2 is enabled, the air outside the gas detecting device 100 is inhaled into the inlet 11 and flows through the gas transportation actuator 2, and the air is discharged from the outlet 12. The gas detector 3 is aligned with the inlet 11, and is located within the casing 1 for detecting an amount of at least one specific gas in the air guided into the casing 1 through the inlet 11. In this embodiment, the gas detector 3 is disposed adjacent to the gas transportation actuator 2 and is located between the gas transportation 2 and the outlet 12. When the gas transportation actuator 2 guides the air to the outlet 12, the air is detected by the gas detector 3 immediately. The driving module 4 is disposed within the casing 1 similarly and is electrically connected to the gas transportation actuator 2 and the gas detector 3. The driving module 4 is configured to control actuations of the gas transportation actuator 2 and the gas detector 3, so that the amount of the specific gas in the air within the casing 1 can be detected by the gas detector 3.

Figure 5A:
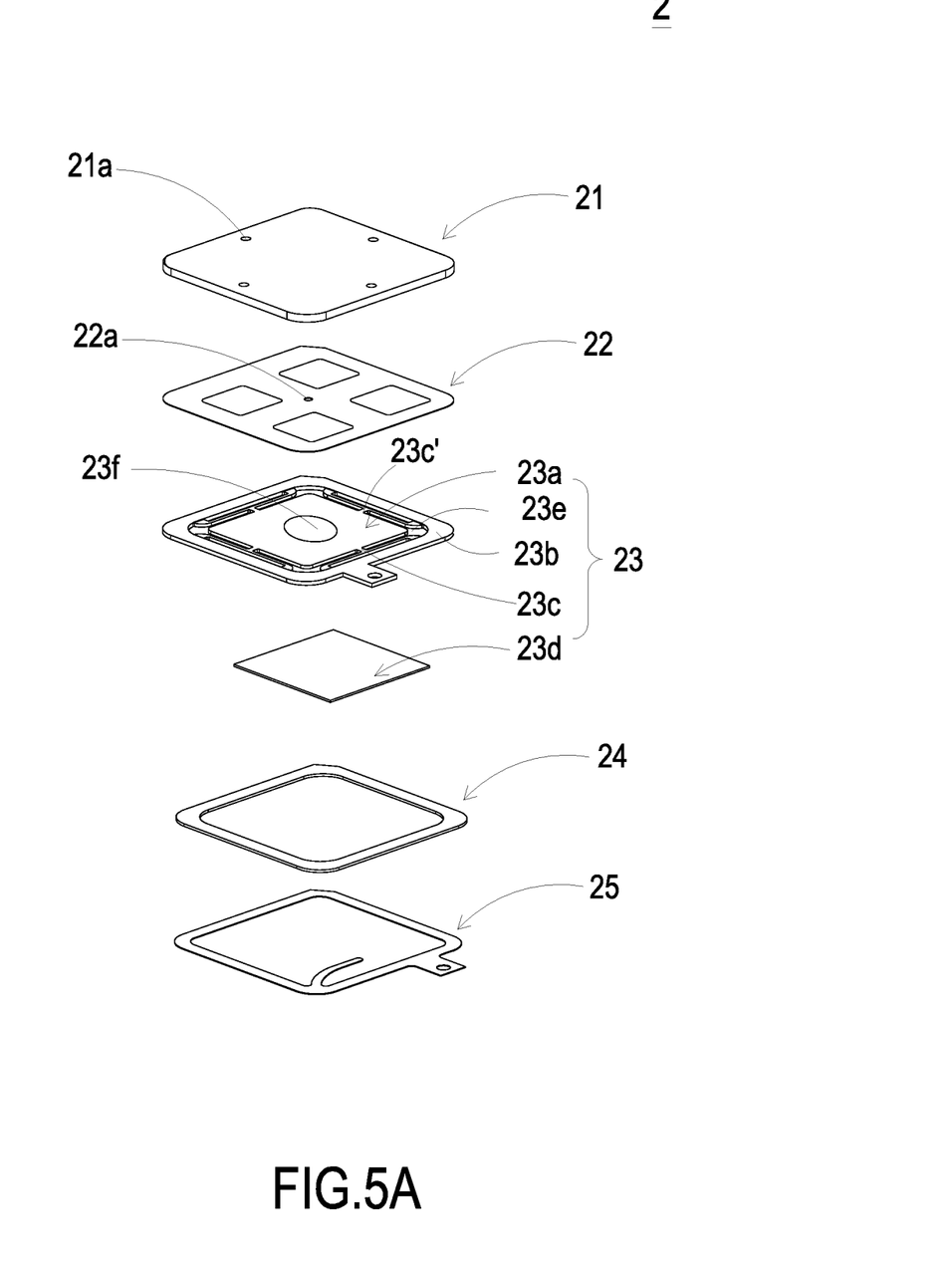
FIG. 5A is a schematic exploded view illustrating the gas transportation actuator of the present disclosure.
Figure 6A:
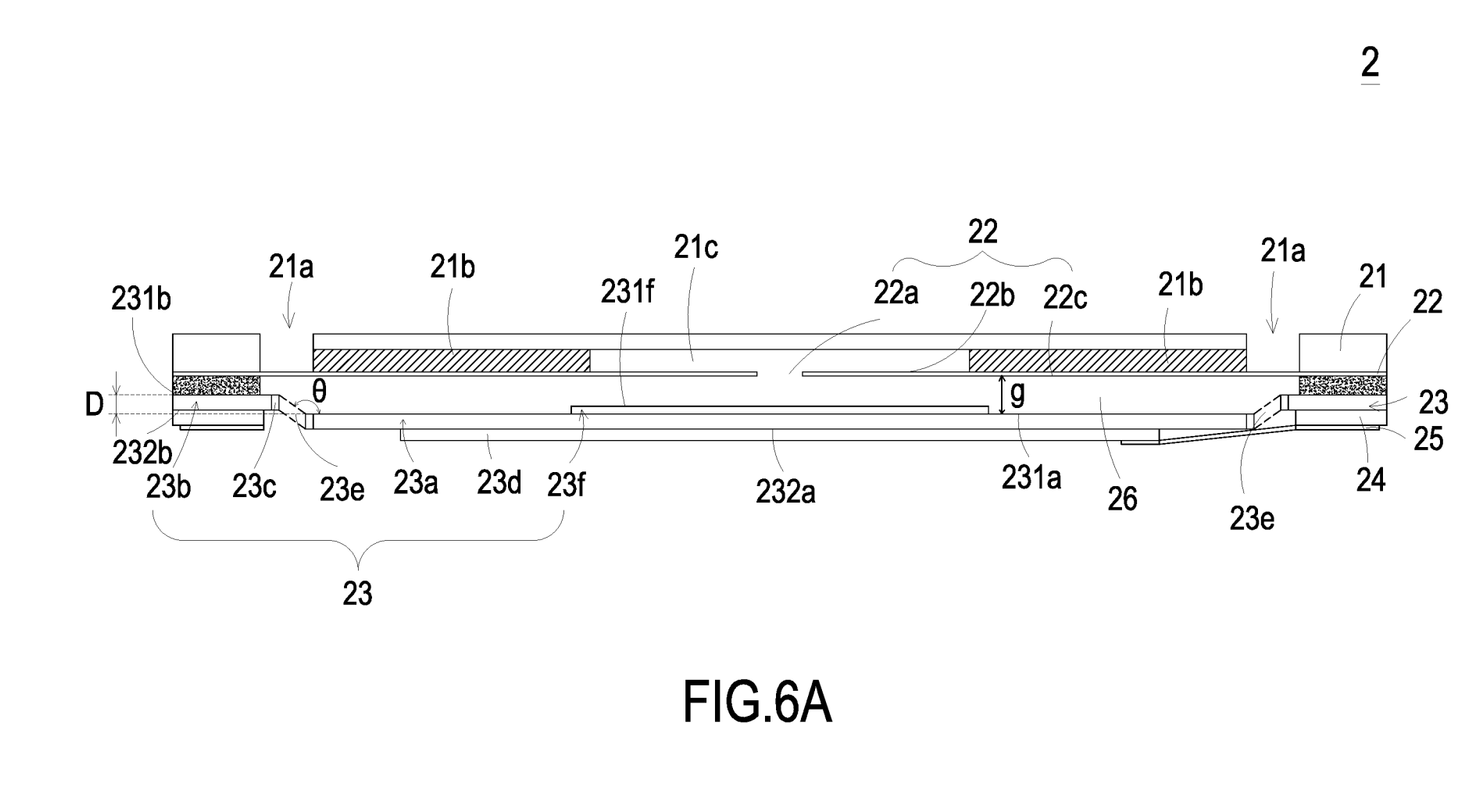
FIG. 6A is a schematic cross-sectional view illustrating the gas transportation actuator of the present disclosure.

Please refer to FIGS. 5A and 6A. The gas transportation actuator 2 includes a gas inlet plate 21, a resonance plate 22, a piezoelectric actuator 23, an insulation plate 24 and a conducting plate 25, which are stacked on each other sequentially. The gas inlet plate 21 has at least one inlet aperture 21a, at least one convergence channel 21b and a convergence chamber 21c. The number of the inlet aperture 21a is the same as the number of the convergence channel 21b. In this embodiment, the number of the inlet aperture 21a and the convergence channel 21b is exemplified by four for each but not limited thereto. The four inlet apertures 21a penetrate through the four convergence channels 21b respectively, and the four convergence channels 21b extend to the convergence chamber 21c.

The resonance plate 22 is assembled on the gas inlet plate 21 by attaching. The resonance plate 22 has a central aperture 22a, a movable part 22b and a fixed part 22c. The central aperture 22a is located in the center of the resonance plate 22 and is aligned with the convergence chamber 21c of the gas inlet plate 21. The region of the resonance plate 22 around the central aperture 22a and corresponding to the convergence chamber 21c is the movable part 22b. The region of the periphery of the resonance plate 22 securely attached on the gas inlet plate 21 is the fixed part 22c.

The piezoelectric actuator 23 includes a suspension plate 23a, an outer frame 23b, at least one bracket 23c, a piezoelectric element 23d, at least one vacant space 23e and a bulge 23f. The suspension plate 23a has a first surface 231a and a second surface 232a opposite to the first surface 231a. The outer frame 23b is disposed around the periphery of the suspension plate 23a. The outer frame 23b has an assembling surface 231b and a bottom surface 232b opposite to the assembling surface 231b. The at least one bracket 23c is connected between the suspension plate 23a and the outer frame 23b for elastically supporting the suspension plate 23a. The vacant space 23e is formed among the suspension plate 23a, the outer frame 23b and the brackets 23c for allowing the gas to go through.

In addition, the first surface 231a of the suspension plate 23a has the bulge 23f. In this embodiment, the formation of the bulge 23f may be completed by using an etching process in which the region between the periphery of the bulge 23f and the periphery of the suspension plate 23a is removed. Accordingly, the bulge 23f of the suspension plate 23a is higher than the first surface 231a, and a stepped structure is formed.

Figure 5B:
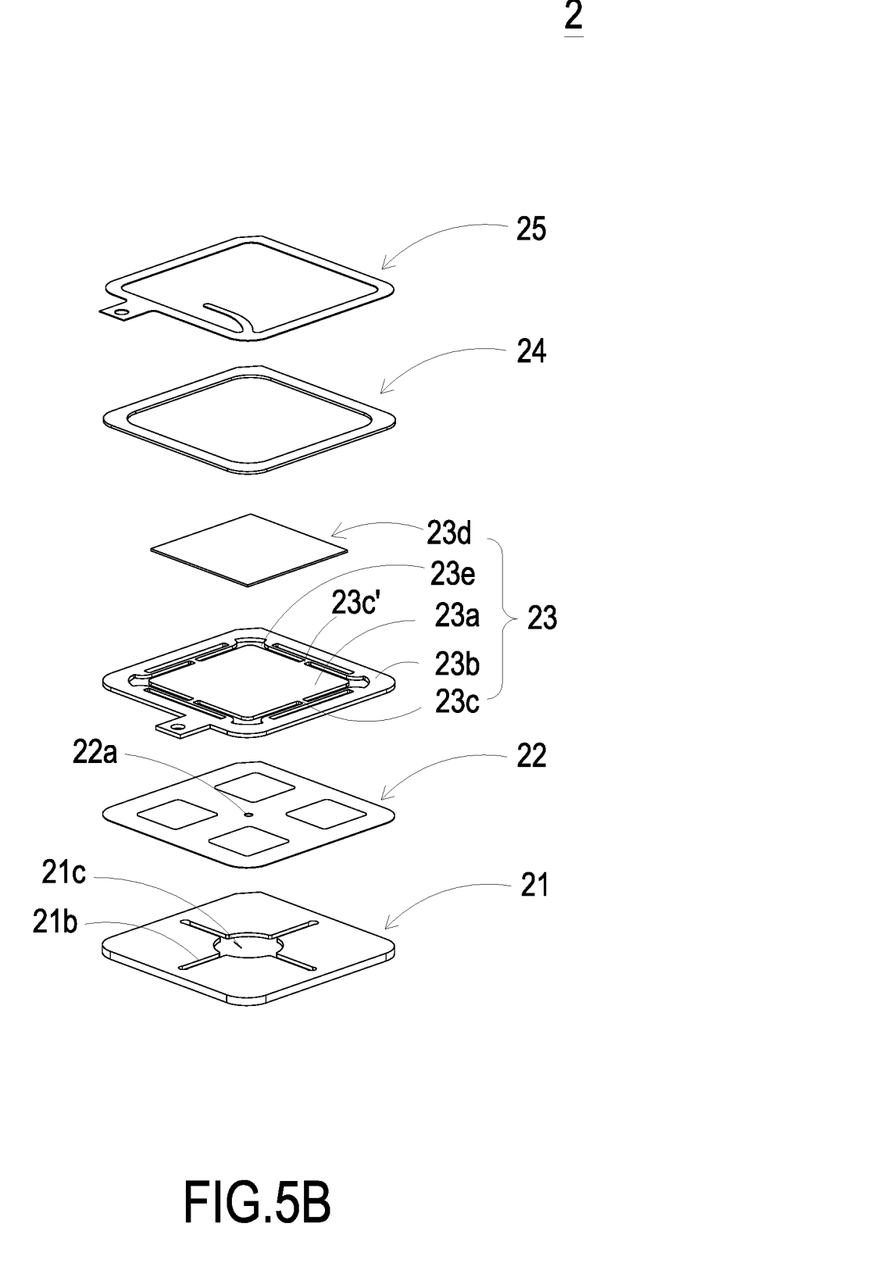
FIG. 5B is a schematic exploded view illustrating the gas transportation actuator of FIG. 5A and taken along another viewpoint.

As shown in FIG. 6A, in this embodiment, the suspension plate 23a may be further processed by using a stamping method. The stamping method makes the suspension plate 23a away from the resonance plate 22 a distance D, which can be adjusted by the bracket 23c, so that the first surface 231a of the suspension plate 23a and the surface 231f of the bulge 23f are not coplanar with the assembling surface 231b of the outer frame 23b. The bracket 23c has a connecting portion 23c' that connects to the suspension plate 23a, as shown in FIG. 5A and FIG. 5B. The connecting portion 23c' of the bracket 23c may not be substantially parallel to the suspension plate 23a. A top surface of the connecting portion 23c' extends away from the resonance plate 22 and connects the first surface 231a which is substantially parallel to the resonance plate 22, and thus there is an angle θ less than 180° at the junction between the bracket 23c and the suspension plate 23a. That is, the first surface 231a of the suspension plate 23a and the surface 231f of the bulge 23f are lower than the assembling surface 231b of the outer frame 23b, and the second surface 232a of the suspension plate 23a is lower than the bottom surface 232b of the outer frame 23b. On the other hand, the piezoelectric element 23d is attached on the second surface 232a of the suspension plate 23a and is disposed opposite to the bulge 23f. In response to an applied driving voltage, the piezoelectric element 23d is subjected to a deformation owing to the piezoelectric effect so as to drive the suspension plate 23a to bend and vibrate. In an embodiment, a small amount of adhesive is applied to the assembling surface 231b of the outer frame 23b, and the piezoelectric actuator 23 is attached on the fixed part 22c of the resonance plate 22 by hot pressing. Therefore, the piezoelectric actuator 23 and the resonance plate 22 are assembled together.

In addition, the insulation plate 24 and the conducting plate 25 are both frame-type thin plate, and the insulation plate 24 and the conducting plate 25 are stacked sequentially and located under the piezoelectric actuator 23. In this embodiment, the insulation plate 24 is attached on the bottom surface 232b of the outer frame 23b of the piezoelectric actuator 23.

Please refer to FIG. 6A. The gas inlet plate 21, the resonance plate 22, the piezoelectric actuator 23, the insulation plate 24 and the conducting plate 25 of the gas transportation actuator 2 are stacked on each other sequentially. A chamber gap g is formed between the first surface 231a of the suspension plate 23a and the resonance plate 22. The chamber gap g is relative to the efficiency of transportation of the gas transportation actuator 2, and thus it is important to maintain a specific chamber gap g for providing a stable efficiency of transportation. In the gas transportation actuator 2 of the present disclosure, the suspension plate 23a is processed by the stamping method so that the first surface 231a of the suspension plate 23a and the surface 231f of the bulge 23f are not coplanar with the assembling surface 231b of the outer frame 23b. That is, the first surface 231a of the suspension plate 23a and the surface 231f of the bulge 23f are lower than the assembling surface 231b of the outer frame 23b, and the second surface 232a of the suspension plate 23a is lower than the bottom surface 232b of the outer frame 23b. In this way, the entire structure may be improved by adopting the stamping method to process the suspension plate 23a, thereby adjusting a chamber space 26 enclosed by the piezoelectric actuator 23 and the resonance plate 22. In other words, a desired chamber gap g may be satisfied by simply adjusting the distance D as described above. The structure design of the adjustable chamber gap g and the manufacturing process are simplified, and the amount of time for the manufacturing process is shortened.

Figure 6B:
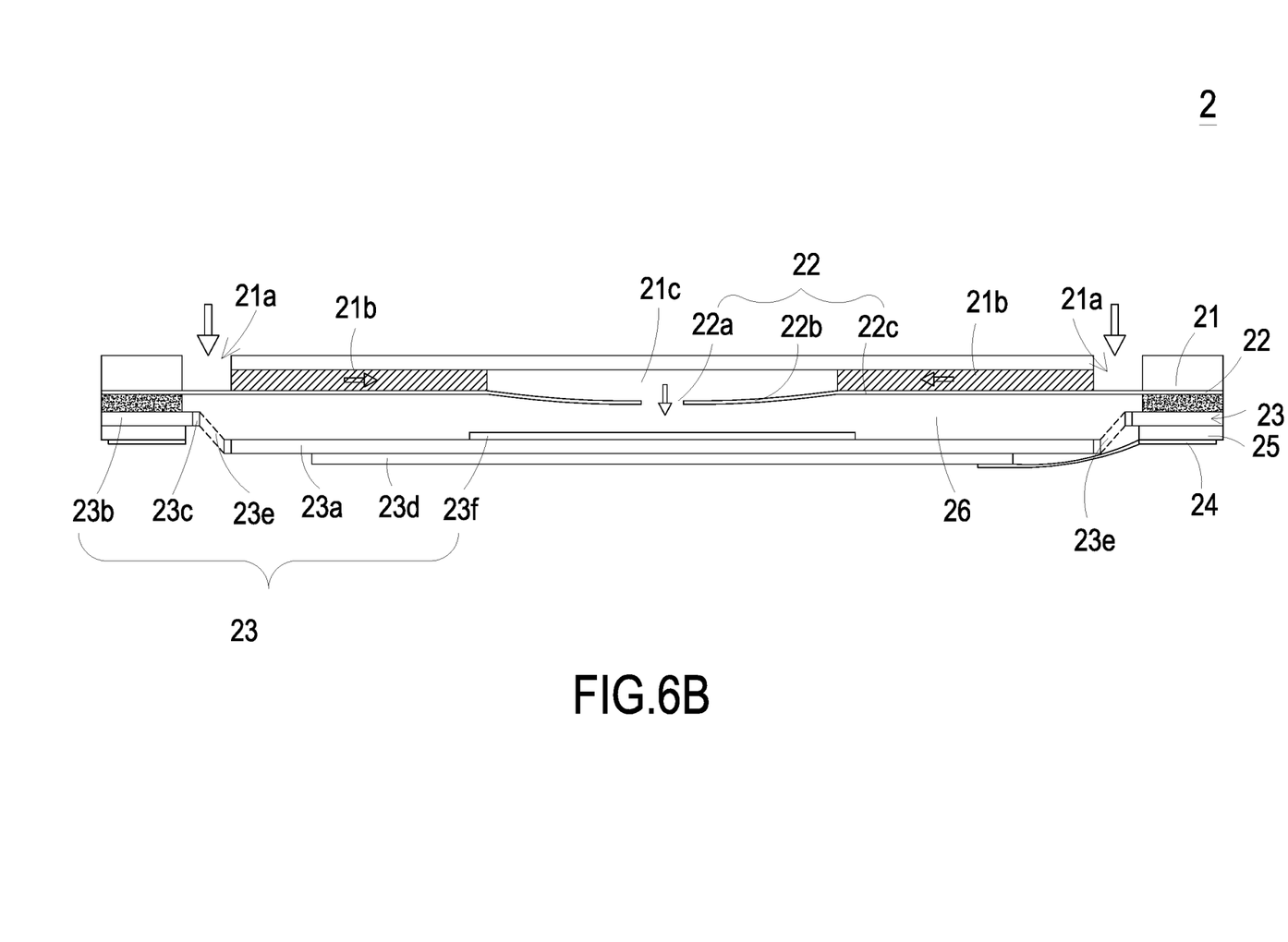
FIGS. 6B to 6D schematically illustrate the actions of the gas transportation actuator according to the embodiment of the present disclosure.
Figure 6C:
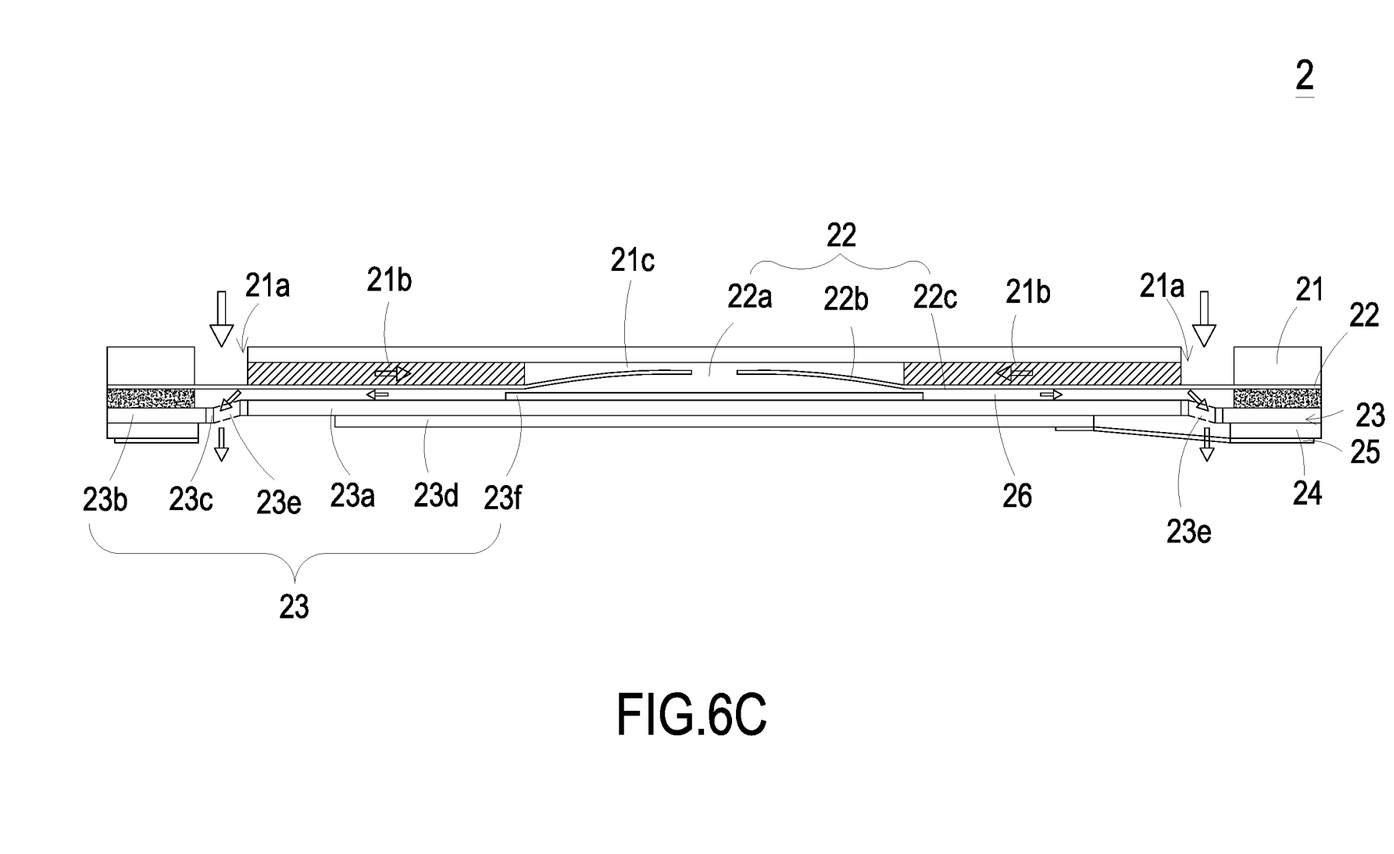
Figure 6D:
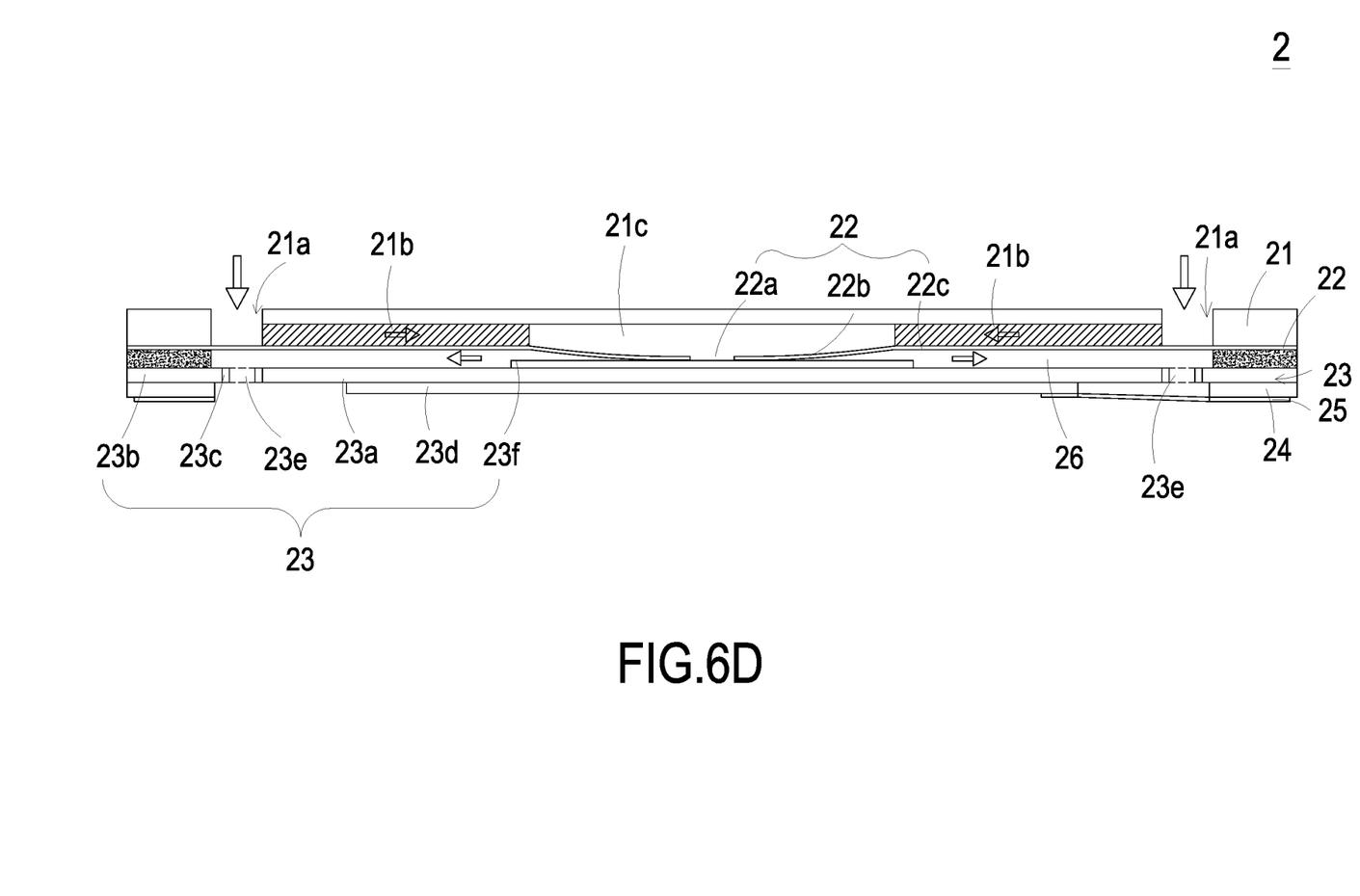

FIGS. 6B to 6D schematically illustrate the actions of the gas transportation actuator 2 of FIG. 6A. Please refer to FIG. 6B. When a driving voltage is applied to the piezoelectric element 23d of the piezoelectric actuator 23, the piezoelectric element 23d deforms to drive the suspension plate 23a to move downwardly. Meanwhile, the volume of the chamber space 26 is increased, and a negative pressure is formed in the chamber space 26 so that the air in the convergence chamber 21c is inhaled into the chamber space 26. At the same time, the resonance plate 22 is in resonance with the piezoelectric actuator 23 to move downwardly, so that the volume of the convergence chamber 21c is expanded. Since the air within the convergence chamber 21c is transported to the chamber space 26, a negative pressure is formed in the convergence chamber 21c. The negative pressure allows the air to be inhaled through the convergence channel 21b and the inlet aperture 21a to the convergence chamber 21c. Please refer to FIG. 6C. The piezoelectric element 23d drives the suspension plate 23a to move upwardly, and the volume of the chamber space 26 is compressed, so that the air within the chamber space 26 is forced to flow downwardly through the vacant space 23e. Thereby, the air transportation efficacy is achieved. Meanwhile, the resonance plate 22 is moved upwardly in resonance with the suspension plate 23a, and the air within the convergence chamber 21c is pushed to move toward the chamber space 26 synchronously. Please refer to FIG. 6D. When the suspension plate 23a is moved downwardly, the resonance plate 22 is moved downwardly in resonance with the suspension plate 23a. Meanwhile, the air within the chamber space 26 is compressed by the resonance plate 22 and is transferred toward the vacant space 23e. The volume of the convergence chamber 21c is expanded, and the air is allowed to flow through the inlet aperture 21a and the convergence channel 21b and converge in the convergence chamber 21c continuously. By repeating the above steps, the air is continuously introduced through the inlet aperture 21a into the gas transportation actuator 2, and then the air is transferred downwardly through the vacant space 23e. Consequently, the efficacy of transferring the air to the gas detector 3 is achieved. The air is continuously provided to the gas detector 3 for detection, thus the efficiency of detecting is increased.

Figure 7:
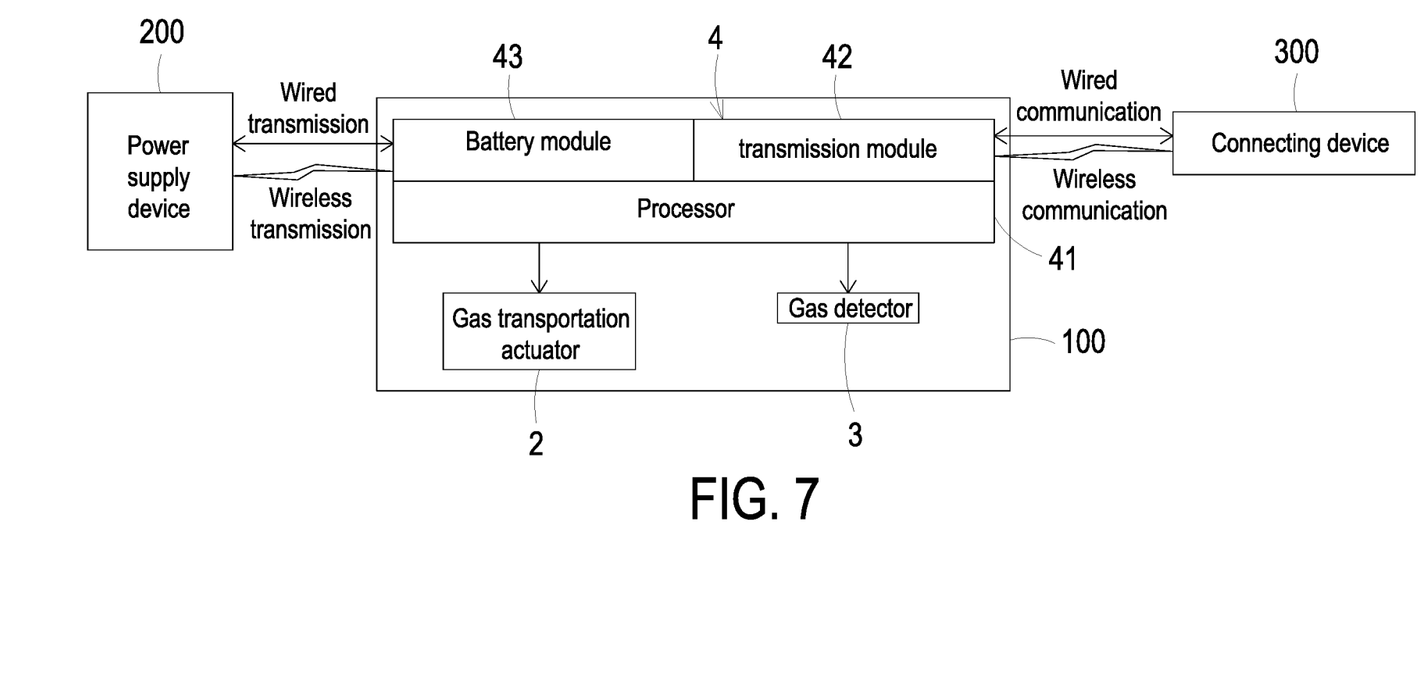
FIG. 7 schematically illustrates the connections of the gas detecting device of the present disclosure and the peripheral equipments.

Please refer to FIGS. 2 and 7. The driving module 4 of the gas detecting device 100 further includes a processor 41, a transmission module 42 and a battery module 43. The processor 41 is electrically connected to the transmission module 42, the gas transportation actuator 2 and the gas detector 3 for controlling actuations of the transmission module 42, the gas transportation actuator 2 and the gas detector 3. The processor 41 analyzes a detecting result from the gas detector 3 and converts the analysis result into a monitoring value. The transmission module 42 transmits the monitoring value to a connecting device 300. The connecting device 300 is configured to display information carried by the monitoring value and announce an alert. The transmission module 42 is a wired transmission module, which may be at least one selected from the group consisting of a USB (Universal Serial Bus) transmission module, a mini-USB transmission module, a micro-USB transmission module and combinations thereof. Alternatively, the transmission module 42 is a wireless transmission module, which may be at least one selected from the group consisting of a Wi-Fi transmission module, a Bluetooth transmission module, a radio frequency identification (RFID) transmission module, a near field communication (NFC) transmission module and combinations thereof. In addition, the connecting device 300 may be at least one selected from the group consisting of a cloud system, a portable electronic device, a computer system and combinations thereof.

The battery module 43 is configured to store and output the electric energy. The battery module 43 provides the electric energy to the processor 41, so that the processor 41 is enabled to control actuations of the gas transportation actuator 2, the transmission module 42 and the gas detector 3. Moreover, the battery module 43 can be connected to a power supply device 200 for receiving and storing the electric energy from the power supply device 200. In particular, the electric energy from the power supply device 200 is transmitted to the battery module 43 via wired transmission technology or wireless transmission technology.

In this embodiment, the gas detector 3 can be at least one selected from the group consisting of a volatile organic compound (VOC) gas detector, an oxygen gas detector, a carbon monoxide gas detector, a carbon dioxide gas detector, a temperature detector, a moisture detector and combinations thereof.

Please refer to FIG. 2. The casing 1 of the gas detecting device 100 further includes a first joint body 1a and a second joint body 1b. The first joint body 1a and the second joint body 1b can be assembled together to form an integral structure. The inlet 11 and the accommodation slot 13 are located on the second joint body 1b. The second joint body 1b may be detachable from the first joint body 1a. As the second joint body 1b is detached from the gas detecting device 100, the gas transportation actuator 2 is allowed to be disposed within and seals the accommodation slot 13. As mentioned above, the first joint body 1a and the second joint body 1b are detachably assembled together to form an integral structure as the casing 1 of the gas detecting device 100. The inlet 11 and the accommodation slot 13 are disposed on the second joint body 1b. The accommodation slot 13 is sealed while the gas transportation actuator 2 is disposed therein. An insulation adhesive plate 5 may be an insulation plate with double-sided viscosity. One side of the insulation adhesive plate 5 may be adhered to the accommodation slot 13. The other side of the insulation adhesive plate 5 may be adhered to the gas transportation actuator 2. The accommodation slot 13 has a sidewall 13a contacting a top surface of the gas inlet plate 21 of the gas transportation actuator. The sidewall 13a may be substantially perpendicular to the top surface of the gas inlet plate 21. The gas inlet plate 21 seals the edge of the sidewall 13a. In this way, the gas transportation actuator 2 can be readily attached and fastened on the accommodation slot 13 by the insulation adhesive plate 5. Owing to the detachable structure design of the second joint body 1b and the fast pasting of the insulation adhesive plate 5, it becomes more convenient to assemble and maintain the gas transportation actuator 2.

From the above descriptions, the present disclosure provides a gas detecting device. The suspension plate of the piezoelectric actuator of the gas transportation actuator is stamped to form the structure including a desired chamber space. Therefore, the efficiency of the gas transportation actuator is controlled more effectively. By increasing the moving speed of the air, the efficiency of detecting the air is improved. The gas detecting device of the present disclosure is industrially valuable.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A gas detecting device, comprising:
   a casing having an inlet, an outlet and an accommodation slot, wherein the inlet and the outlet are in fluid communication with each other, and the accommodation slot is disposed under the inlet and is in fluid communication with the inlet;
   a gas transportation actuator, wherein the gas transportation actuator is disposed within and seals the accommodation slot, and the gas transportation actuator is enabled to introduce air thereinto through the inlet and discharge the air through the outlet;
   a gas detector disposed under the accommodation slot and configured to detect an amount of a specific gas in the air discharged by the gas transportation actuator; and
   a driving module disposed within the casing and configured to control the actuations of the gas transportation actuator and the gas detector, whereby the gas detector detects the amount of the specific gas in the air.

2. The gas detecting device according to claim 1, wherein the gas transportation actuator comprises:
   a gas inlet plate having at least one inlet aperture, at least one convergence channel and a convergence chamber, wherein the at least one inlet aperture allows the air to flow in, the convergence channel is disposed corresponding to the inlet aperture and guides the air from the inlet aperture toward the convergence chamber;
   a resonance plate having a central aperture and a movable part, wherein the central aperture is aligned with the convergence chamber, and the movable part surrounds the central aperture; and
   a piezoelectric actuator aligned with the resonance plate, wherein a chamber gap is formed between the resonance plate and the piezoelectric actuator to define a chamber space, so that the air from the at least one inlet aperture of the gas inlet plate is converged to the convergence chamber along the at least one convergence channel and flows through the central aperture of the resonance plate when the piezoelectric actuator is enabled, whereby the air is further transferred through a resonance between the piezoelectric actuator and the movable part of the resonance plate.

3. The gas detecting device according to claim 2, wherein the piezoelectric actuator comprises:
   a suspension plate having a first surface and a second surface, wherein the first surface has a bulge;
   an outer frame arranged around the suspension plate and having an assembling surface;
   at least one bracket connected between the suspension plate and the outer frame for elastically supporting the suspension plate; and
   a piezoelectric element attached on the second surface of the suspension plate, wherein when a voltage is applied to the piezoelectric plate, the suspension plate is driven to undergo a bending vibration,
   wherein the at least one bracket is formed between the suspension plate and the outer frame, the first surface of the suspension plate is not coplanar with the assembling surface of the outer frame, and the chamber gap is maintained between the first surface of the suspension plate and the resonance plate.

4. The gas detecting device according to claim 2, wherein the gas transportation actuator comprises a conducting plate and an insulation plate, and the gas inlet plate, the resonance plate, the piezoelectric actuator, the insulation plate and the conducting plate are stacked sequentially.

5. The gas detecting device according to claim 1, wherein the driving module comprises a processor and a transmission module, wherein the processor controls the actuations of the transmission module, the gas transportation actuator and the gas detector, the processor analyzes and converts a detecting result from the gas detector into a monitoring value, the monitoring value is transmitted to a connecting device by the transmission module, and the connecting device is configured to display information carried by the monitoring value and announce an alert.

6. The gas detecting device according to claim 5, wherein the transmission module is at least one selected from the group consisting of a wired transmission module and a wireless transmission module.

7. The gas detecting device according to claim 6, wherein the wired transmission module is at least one selected from the group consisting of a USB transmission module, a mini-USB transmission module, a micro-USB transmission module and combinations thereof.

8. The gas detecting device according to claim 6, wherein the wireless transmission module is at least one selected from the group consisting of a Wi-Fi transmission module, a Bluetooth transmission module, a radio frequency identification transmission module, a near field communication transmission module and combinations thereof.

9. The gas detecting device according to claim 5, wherein the connecting device is at least one selected from the group consisting of a cloud system, a portable device, a computer system and combinations thereof.

10. The gas detecting device according to claim 5, wherein the driving module further comprises a battery module configured to store and output electric energy, the battery module provides the electric energy to the processor so that the processor is enabled to control the actuations of the gas transportation actuator, the transmission module and the gas detector, and the battery module is connected to a power supply device for receiving and storing the electric energy from the power supply device.

11. The gas detecting device according to claim 10, wherein the electric energy from the power supply device is transmitted to the battery module for storage via a wired transmission technology.

12. The gas detecting device according to claim 10, wherein the electric energy from the power supply device is transmitted to the battery module for storage via a wireless transmission technology.

13. The gas detecting device according to claim 1, wherein the gas detector comprises a volatile organic compound gas detector.

14. The gas detecting device according to claim 1, wherein the casing comprises a first joint body and a second joint body, wherein the first joint body and the second joint body are assembled together to form an integral structure, the inlet and the accommodation slot are disposed on the second joint body, and the second joint body is detachable from the first joint body, thereby allowing the gas transportation actuator to be disposed within and seal the accommodation slot.

15. The gas detecting device according to claim 14, wherein the gas transportation actuator is assembled and attached on the accommodation slot by an insulation adhesive plate with double-sided viscosity, and the accommodation slot is sealed.

* * * * *